United States Patent
Billet et al.

(10) Patent No.: US 6,183,253 B1
(45) Date of Patent: Feb. 6, 2001

(54) ENDODONTIC INSERT PRE-IMPREGNATED WITH REINFORCING FIBRES FOR FILLING THE DENTAL CANAL

(76) Inventors: Gilles Billet, 32 avenue d'Haussez, F-38500 Voiron; Bruno Clunet-Coste, Tolvon, F-38960 Saint Etienne de Crossey; André Collombin, 22 rue du Lavoir de Criel; Bernard Maneuf, Hameau de Vouise, both of F-38500 Voiron, all of (FR); Leif Siguard Nordvall, PO Box 4199, SE-31104 Glommen (SE)

(*) Notice: Under 35 U.S.C. 154(b), the term of this patent shall be extended for 0 days.

(21) Appl. No.: 09/254,434
(22) PCT Filed: Sep. 15, 1997
(86) PCT No.: PCT/FR97/01622
  § 371 Date: Mar. 9, 1999
  § 102(e) Date: Mar. 9, 1999
(87) PCT Pub. No.: WO98/11842
  PCT Pub. Date: Mar. 26, 1998

(30) Foreign Application Priority Data
Sep. 17, 1996 (FR) .................................................. 96 11524

(51) Int. Cl.⁷ ........................................................ A61G 5/02
(52) U.S. Cl. ................................................ 433/81; 433/224
(58) Field of Search ............................. 433/81, 102, 224, 433/220

(56) References Cited

U.S. PATENT DOCUMENTS

| 4,425,094 | 1/1984 | Tateosian et al. |
| 4,936,776 | 6/1990 | Kwiatkowski . |
| 4,952,150 | * 8/1990 | Schiwiora et al. .................... 433/220 |
| 5,074,792 | * 12/1991 | Bernadat .......................... 433/224 X |
| 5,797,748 | * 8/1998 | Reynaud et al. ...................... 433/224 |
| 5,816,816 | * 10/1998 | Scharf .............................. 433/224 X |
| 5,890,904 | * 4/1999 | Reynaud et al. ...................... 433/220 |
| 5,915,970 | * 6/1999 | Sicurelli, Jr. et al. ............... 433/220 |

FOREIGN PATENT DOCUMENTS

| 562 605 | 6/1975 | (CH) . |
| 38 25 601 A1 | 3/1989 | (DE) . |
| 0 432 001 A1 | 6/1991 | (EP) . |
| WO 96/15731 | 5/1996 | (WO) . |

\* cited by examiner

*Primary Examiner*—Nicholas D. Lucchosi
(74) *Attorney, Agent, or Firm*—Ollif & Berridge, PLC

(57) ABSTRACT

The invention concerns an insert for filling the dental canal comprising means for anatomically and physiologically filling up the root canal 1, comprising a ductile and resilient core 10 made of a polymerised composite material, sheathed in one or several sleeves 14, 15 made of a composite material pre-impregnated with resin, being in a first pasty state previous to polymerisation so as to make the insert flexible and malleable before and during its introduction into the root canal 1. Said material is then polymerized at will by cross-linking means to be in a second polymerized state after the insert has been introduced in said canal. The upper part 17 of the insert which emerges from the root canal 1, can advantageously be used as prop or pivot for a coronal reconstitution. Thus, the same material is used for filling the root canal and for reinforcing the residual structures of the tooth. The canal obturator and the anchoring pivot are made of one and the same material.

19 Claims, 1 Drawing Sheet

ENDODONTIC INSERT PRE-IMPREGNATED WITH REINFORCING FIBRES FOR FILLING THE DENTAL CANAL

BACKGROUND OF THE INVENTION

The invention relates to an insert for filling the dental canal comprising means for anatomically and physiologically filling up the root canal.

STATE OF THE TECHNIQUE

In dentistry, and in particular in endodonty, the root canals must be hermetically obturated. In the prior art, certain specific materials are generally used, such as gutta-percha, or zinc/eugenol oxide pastes, or for example Bakelite resins in the form of bi-component preparations, which are inserted in the canal by mechanical means.

These known materials have to be partially removed when the coronal part of the tooth has to be reconstituted. A pivot is generally inserted and sealed in the root canal after shaping to act as anchoring part for a coronal reconstitution. The coronal reconstitution phase is carried out in a different session from that of the canal obturation.

According to the document CH-A-562,605, the pivots can be made of metallic material and are each provided with a thread designed for screwing the base of the pivot into the root canal.

Pivots made of pre-fabricated composite material, which may be reinforced by fibres, are described in the documents U.S. Pat. No. 4,936,776, DE-A-3,825,601 and EP-A-0,432,001. Each pivot presents a straight finished shape and a rigid structure before insertion in the canal. Should a root be curved, the pivot can therefore in no case follow this curving, and the practician then has to enlarge the canal to enable the pivot to be fitted. The work of enlarging the canal is liable to reduce the solidity of the root, with non-negligible risks of perforation.

In all these known techniques, the anchoring pivot is generally made of a different material from that of the canal filling, and the joining interface between the pivot and the canal filling material forms a fragilised zone subjected to large mechanical stresses in the course of chewing.

OBJECT OF THE INVENTION

A first object of the invention is to achieve a canal filling insert of high mechanical strength, and able to be easily inserted in the root canal.

A second object of the invention relates to a process enabling canal filling and construction of an anatomical and physiological root anchoring to be carried out in a single operation.

The endodontic insert according to the invention is characterized in that the filling means comprise a ductile or malleable core made of a composite material in polymerised state, sheathed in one or more sleeves made of a composite material pre-impregnated with resin, and being in a first pasty state prior to polymerisation so as to make the insert material ductile and malleable before and during introduction of the insert into the root canal, said material then being able to be polymerised as required by cross-linking means to change to a second polymerised state after the insert has been inserted in said canal.

According to a preferred embodiment, the core of composite material comprises an organic matrix reinforced by fibres and/or organic or mineral particles, or both. The organisation of the core reinforcing fibres may be unidirectional, pluridirectional, or random.

According to one feature of the invention, the core is hollow and comprises an internal duct for injection of a glue-based sealing agent into the canal. The wall of the core is advantageously porous to allow passage of the glue, introduced under controlled pressure via the duct.

According to another feature of the invention, the paste constituting the sleeve or sleeves comprises an organic matrix reinforced by fibres or organic or mineral particles, of the same nature and structure as those of the core.

The external sleeve is formed by a sheath made of composite material of the same type as the internal sleeve or sleeves, said sheath being malleable and acting as container for all the materials of the core and of the sleeves.

The structure of the fibres of the external sheath is arranged to allow the excess resin to pass by extrusion as insertion of the insert in the canal takes place. The excess resin mixes with the sealing agent glue to seal the small dentinary canals of the root.

The upper part of the insert which emerges from the root canal can advantageously act as prop or pivot for a coronal reconstitution. The same material is thus used for filling the root canal and for reinforcing the residual structures of the tooth. The canal obturator and the anchoring pivot are made of one and the same material.

The insert is presented in the form of a manufactured product stored away from electromagnetic radiation in a sealed sachet at a temperature of less than 37° C.

After the insert has been fitted in the canal, polymerisation by the action of the cross-linking means can be performed, by electromagnetic radiation, and/or light rays, and/or by thermal effect. Mass polymerisation of the insert and of the sealing agent glue is performed at the same time which enhances the mechanical strength of the assembly.

DESCRIPTION OF THE FIGURES

Other advantages and features of the invention will become more clearly apparent from the following description of an embodiment given as a non-restrictive example only, and represented in the accompanying drawings, in which.

DESCRIPTION OF A PREFERRED EMBODIMENT

Figure 1:
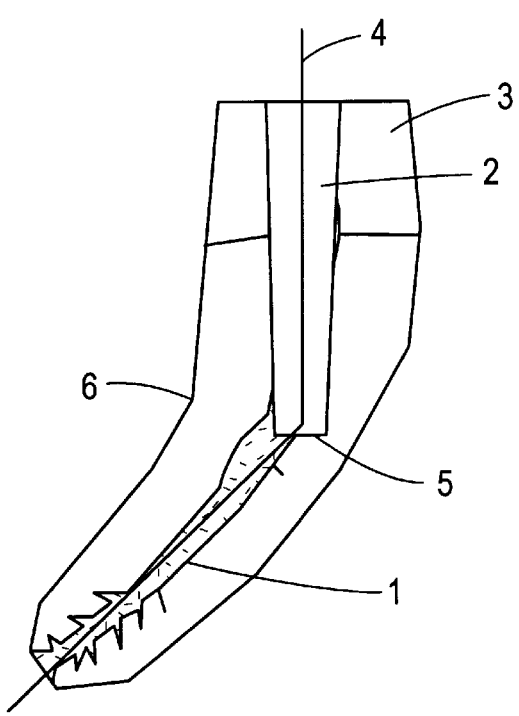
FIG. 1 shows a schematic vertical sectional view of a coronal tooth reconstitution, and of a root equipped with a pivot according to the prior art.

With reference to FIG. 1, the bottom part of the root canal 1 of the root 6 is filled with a filling material, and the upper part has to be enlarged and shaped to enable a pivot 2 to be fitted acting as anchoring part for the coronal reconstitution 3. The materials constituting the pivot 2 and filling material are different. The joining interface of the pivot 2 and filling material may present a fragilised zone 5, in particular in the case of perforation of the canal.

Figure 2:
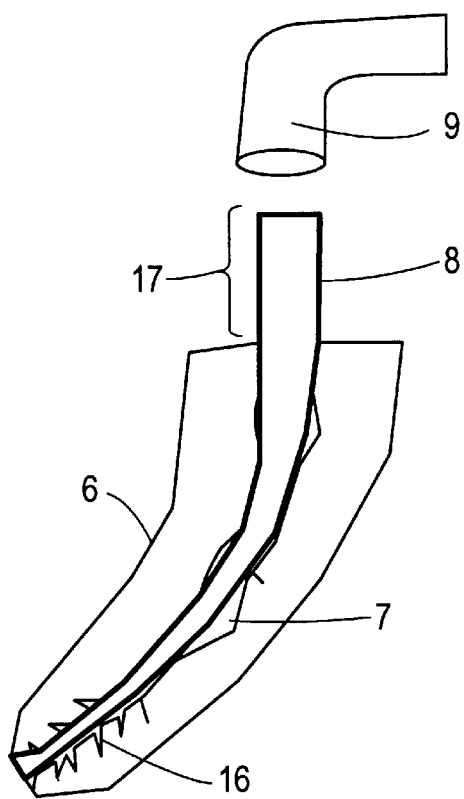
FIG. 2 is an identical view to FIG. 1, with an endodontic canal filling insert according to the invention.
Figure 3:
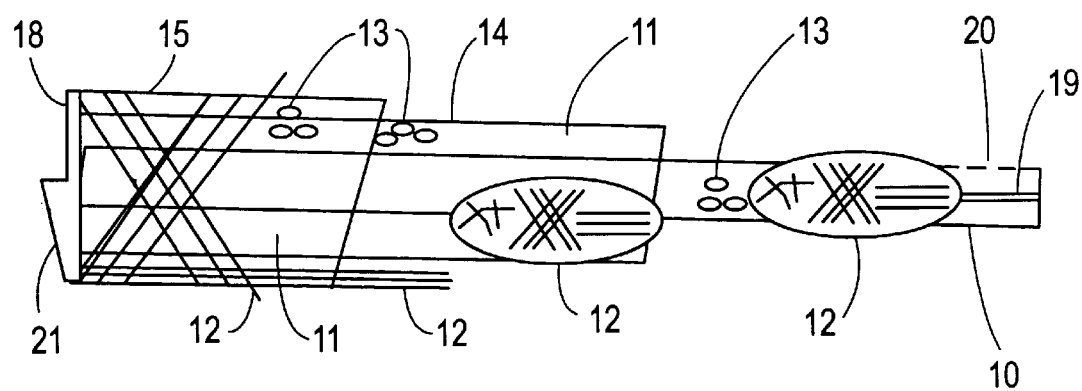
FIG. 3 represents a schematic view on an enlarged scale of the insert of FIG. 2.

In FIGS. 2 and 3, implementation of the insert according to the invention takes place as follows:

The dental canal 1 is first shaped, and cleaning and disinfecting thereof is performed. The walls of the canal 1 are treated by an acid attack, then rinsed and dried, according to the usual bonding protocols used in adhesive dentistry.

A hydrophile photo-polymerisable glue-based sealing agent 7 is introduced into the canal. The insert filling material 8 is inserted in the canal 1 and follows the twists and turns thereof by plastic deformation.

The assembly formed by the glue 7 and filling material 8 is then polymerised by means for example of a photo-polymerising lamp 8, sealing the canal 1 and the small accessory canals 16.

The insert material 8 comprises a semi-rigid and malleable core 10 made of composite material in polymerised state, formed by an organic matrix 11 and organic or mineral or organo-mineral reinforcement fibres 12, or particles 13 formed for example by pyrolytic silica, glass, ceramic, borosilicate or ceramic glasses, barium-aluminium glass, or strontium aluminium. Other particles 13 can be used, notably particles of radio-opaque heavy metals such as nobium, tin, titanium, and also organic or mineral pigments.

The organisation of the fibres can be uniaxial or multiaxial or woven tissues of fibres may moreover be used.

The fibres 12 can be long fibres or micro-fibrils. A single fibre can also be used.

The core 10 can advantageously be hollow and act as internal canal 19 for injection of the sealing agent glue 7. The wall of the core 10 can also have a porous structure 20 to let the glue 7 injected via the internal canal 19 exude.

The fibres 12 of the core 1 0 can be chosen from any sort of fibre, in particular glass, aramid, polyester, or boron fibres, allowing electromagnetic radiation to pass. They must in particular be permeable to light rays to act as light guide.

All these charges are treated before being incorporated in the organic matrix by means of organo-silane composites such as aryloxy-silanes and/or halogeno-silanes, without limitation.

The organic matrix is chosen from the group formed by dimethacrylate-base aromatic resins, polymethacrylates, methacrylates, methacrylate-urethanes, polyacetates, polycarbonates, epoxy-base aromatic resins, or polyester resins.

The core 10 acts as prop for the material and is coated with one or more sleeves 14 made of pre-impregnated composite material in a pasty pre-polymerisation state, polymerisation of which material can be performed by electromagnetic radiation.

The first sleeve 14 is formed by a paste of composite material in pre-polymerisation state and comprising an identical organic matrix to that of the core 10 and of the reinforcements 12, 13 of the same nature. The organic matrix of the sleeve(s) 14 contains photosetting components such as dicetones, in particular diacetyl and/or quinones such as camphoroquinone and acenaphene quinone sensitive to visible light, and also accelerators, in particular amines. The organic matrix can thus be cross-linked by lighting by visible light.

Another solution consists in the parts in the non-polymerised state of the composite material of the sleeves 14, and also the glue 7, being kept at a temperature of less than 37° C., and polymerising by thermal effect, alone or combined with electromagnetic radiation, when the material reaches the temperature of the human body.

The sleeves 14 are kept in shape by a sheath 15 itself made of composite material in the pre-polymerisation state. The sheath 15 is composed of the same organic matrix 11 as the sleeves and of the same reinforcements 12, 13. However the reinforcement fibres 12 of the sheath 15 are organised as tissues of fibres forming a spatial geometry of the material. The organisation of the fibres may also be unidirectional and even parallel to the axis of the insert.

The sheath 15 acts as container for the insert material and can be deformed by simple pressure. It can let excess resin pass through its meshes when the insert is fitted in the canal 1. The sheath 15 enables all of the material to transmit the rays, and in particular light rays, necessary for photo-polymerisation of the bonding resins. The sheath 15 is an essential element for electromagnetic radiation diffusion and enables an equal lighting to be achieved inside the dental canal 1 in case of light insolation.

The assembly formed by the central core 10, the intermediate sleeves 14 and the external sheath 15 can be soldered and/or sealed at one end 18 of the insert for the material not to come unbound when its insertion in the root canal 1 takes place. The end 18 can advantageously be rounded 21 to prevent any blocking or jamming when the insert is inserted in the root canal 1.

One of the essential points of the invention is that the whole of the insert material remains ductile and malleable so long as cross-linking has not been voluntarily caused. The insert can therefore follow the exact shape of all the twists and curves of the root canal 1.

A second important point is that the volume of the material surrounding the central core 10 can take the shape of the volume of the dental canal, by simple deformation, and by expulsion of a part of the resin as the insert is progressively inserted in the canal 1.

A third important point is that when cross-linking of the organic matrix is performed, the whole of the insert material will polymerise simultaneously.

Furthermore, the resin of the sealing agent 7 previously or simultaneously inserted in the dental canal 1 before the insert is introduced will also polymerise, sealing the small accessory dentinary canals 16 in particular by means of the light diffusion performed by the sheath 15, sleeves 14 and core 10 of the insert.

A fourth point is that, when the practician has taken care to let the insert emerge from the dental root 6, the emerging part 17 of the insert will act as reinforcement pillar for reconstruction of the tooth 3 by conventional techniques. The dental canal filling insert which forms the subject of the invention also plays the role of reconstitution prop.

The process according to the invention for anatomic and physiological filling based on a manufactured article performs filling of the root canals 16 and achievement of a reinforcement root anchoring in a single operation.

The mechanical characteristics of the insert after cross-linking are identical to those described in the document WO 96/15731. The filling insert therefore also has a similar mechanical behaviour to root dentine.

However, the fact of following the twists and turns of the canal 1 resulting from its structure ensures an additional mechanical root anchoring and prevents disinsertion by traction or rotation.

What is claimed is:

1. An insert for filling a dental canal comprising a ductile or malleable core made of a composite material in polymerised state, said core being sheathed in at least one sleeve made of a composite material pre-impregnated with resin, said composite material of said at least one sleeve being in a first pasty state prior to polymerisation such that the insert is ductile and malleable before and during its introduction into the root canal, wherein said composite material of said at least one sleeve is able to be polymerised with cross-linking to change the composite material to a second polymerised state after the insert has been inserted in said canal.

2. The insert for filling the dental canal according to claim 1, wherein the core comprises an organic matrix with reinforcing fibres and/or organic or mineral particles.

3. The insert for filling the dental canal according to claim 2, wherein the organization of the fibres of the core is at least one of unidirectional, pluridirectional and random.

4. The insert for filling the dental canal according to claim 1, wherein the core is arranged as a light guiding duct, enabling the passage of electromagnetic or light radiation.

5. The insert for filling the dental canal according to claim 1, wherein the core is formed by a single filament.

6. The insert for filling the dental canal according to claim 1, wherein the core is hollow and comprises an internal duct for injection of a glue-based sealing agent.

7. The insert for filling the dental canal according to claim 6, wherein the wall of the core is porous to allow passage of the glue-based sealing agent, introduced under controlled pressure via the duct.

8. The insert for filling the dental canal according to claim 2, wherein the paste constituting the at least one sleeve comprises an organic matrix reinforced by fibres or by organic or mineral particles.

9. The insert for filling the dental canal according to claim 8, the at least one sleeve including an external sleeve and at least one internal sleeve, wherein the external sleeve is formed by a sheath made of composite material of the same type as the internal sleeve or sleeves, said sheath being malleable and acting as container for all the materials of the core and of the sleeves.

10. The insert for filling the dental canal according to claim 9, wherein the fibres of the core and of the sleeves are organized according to unidirectional orientations, and the volume of the sleeves and of the external sheath is modifiable by simple pressure.

11. The insert for filling the dental canal according to claim 9, wherein the external sheath is a light channel enabling a light ray to pass.

12. The insert for filling the dental canal according to claim 9, wherein the assembly constituting the insert is soldered or sealed at one end in such a way that the material does not come unbound when its insertion in the root canal takes place.

13. The insert for filling the dental canal according to claim 12, wherein the soldered end part of the insert is rounded to facilitate said insertion.

14. The insert for filling the dental canal according to claim 9, wherein the structure of the fibres of the external sheath is arranged to allow excess resin to pass by extrusion as insertion of the insert in the canal takes place, and the extrusion of said excess resin mixes with the glue-based sealing agent to seal small dentinary canals of the root.

15. The insert for filling the dental canal according to claim 1, wherein part of the insert emerging from the root canal acts as a prop or pivot for a coronal reconstitution.

16. The insert for filling the dental canal according to claim 1, the insert is a manufactured product stored away from electro-magnetic radiation in a sealed sachet at a temperature of less than 37° C.

17. The insert for filling the dental canal according to claim 1, wherein the composite material of the at least one sleeve is polymerised with cross-linking by electromagnetic radiation or by light rays or by thermal effect.

18. The insert for filling the dental canal according to claim 17, wherein mass polymerisation of the insert and of the glue-based sealing agent is performed at the same time.

19. The insert for filling the dental canal according to claim 8, wherein the organic matrix reinforced by fibers or by organic or mineral particles of said paste is of the same nature and structure as those of the core.

* * * * *